United States Patent [19]

Toth et al.

[11] Patent Number: 4,510,338
[45] Date of Patent: Apr. 9, 1985

[54] RESORCIN DERIVATIVES, PROCESS FOR THEIR PREPARATION AND PHARMACEUTICAL COMPOSITIONS CONTAINING THEM

[75] Inventors: Edit Toth; Jozsef Torley; Gyorgy Fekete; Laszlo Szporny; Laszlo Vereczkey; Eva Palosi; Imre Klebovich; Pal Vittay; Sandor Gorog; Istvan Hajdu, all of Budapest, Hungary

[73] Assignee: Richter Gedeon Vegyeszeti Gyar Rt., Budapest, Hungary

[21] Appl. No.: 565,839

[22] Filed: Dec. 27, 1983

[30] Foreign Application Priority Data

Dec. 28, 1982 [HU] Hungary ............................. 4189/82

[51] Int. Cl.³ ............................................. C07C 39/11
[52] U.S. Cl. ..................... 568/766; 568/744; 568/745; 568/765; 568/775; 568/809; 568/811; 568/812
[58] Field of Search ............... 568/745, 763, 809, 811, 568/744, 747, 765, 775, 812, 716

[56] References Cited

U.S. PATENT DOCUMENTS 2,247,404  7/1941  Perkins et al. ........................ 568/745
2,719,866  10/1955  Gerzon ................................ 568/744
3,943,122  3/1976  Sailer .................................. 568/622
4,094,908  6/1978  Toths et al. .......................... 568/809

*Primary Examiner*—Werren B. Lone
*Attorney, Agent, or Firm*—Karl F. Ross; Herbert Dubno

[57] ABSTRACT

The invention relates to new resorcin derivatives of the formula (I)

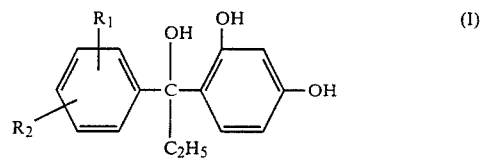

wherein $R_1$ and $R_2$ independently represent hydrogen, halogen, trihalomethyl, alkyl having from one to 3 carbon atoms or alkoxy having from one to 3 carbon atoms.

According to another aspect of the invention there are provided processes for the preparation of these compounds.

The compounds of the formula (I) are pharmacologically active. In particular, they are suitable for the treatment of acute ethanolic intoxication. Pharmaceutical compositions containing them as active ingredient are also within the scope of the invention.

4 Claims, No Drawings

RESORCIN DERIVATIVES, PROCESS FOR THEIR PREPARATION AND PHARMACEUTICAL COMPOSITIONS CONTAINING THEM

This invention relates to new resorcin derivatives. More particularly, the invention concerns new resorcin derivatives of the formula (I)

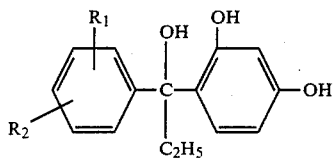

wherein $R_1$ and $R_2$ independently represent hydrogen, halogen, trihalomethyl, alkyl having from one to 3 carbon atoms or alkoxy having from one to 3 carbon atoms.

The invention further relates to a process for the preparation of these compounds and pharmaceutical compositions containing them as active ingredient.

The term "halogen" as used herein embraces all of the halogens, and may be fluorine, chlorine, bromine or iodine, preferably fluorine or chlorine.

The term "alkyl having from one to 3 carbon atoms" refers to straight or branched chained aliphatic hydrocarbon groups containing from one to 3 carbon atoms.

The term "alkoxy having from one to 3 carbon atoms" is used herein to refer to straight or branched chained alkoxy groups containing from one to 3 carbon atoms, preferably methoxy.

The trihalomethyl groups may contain any of the halogens listed above, preferably fluorine.

Compounds of analogous structure are disclosed for example in the following references: C.A. 22, 410[1]; 35, 1781[2]; 40, 4712[5]; 42, P 1015 b; 47, 9548 e; 50, 12390 c; 50, 2509 i; 55, 17915 e; 55, 15413 b; 75, P 103682 b; 76, P 119921 k; 82, 16477 g; 90, 86082 g; 92, 52927 b; none of these citations does, however, mention any pharmaceutical activity for the disclosed compounds.

According to a further aspect of the present invention there is provided a process for the preparation of the compounds of the formula (I), wherein $R_1$ and $R_2$ each have the same meanings as defined above, which process comprises (a) reacting 2',4'-dihydroxy-propiophenone with a Grignard compound of the formula (II)

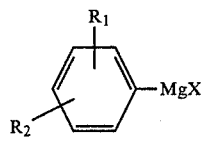

wherein $R_1$ and $R_2$ are as defined above, and X is halogen; or (b) reacting 2',4'-dihydroxy-propiophenone with an organometallic compound of the formula (III)

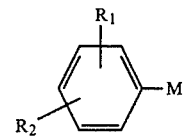

wherein $R_1$ and $R_2$ are as defined above, and M is an alkali metal, preferably lithium, sodium or potassium; or (c) reacting a benzophenone of the formula (IV)

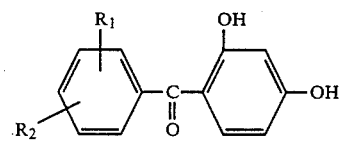

wherein $R_1$ and $R_2$ are as defined above, with an organometallic compound containing an ethyl group, preferably an ethyl magnesium halide or ethyl lithium.

The starting compounds are known or can be prepared by methods known in the art. The starting substances of the formula (II) are obtained by preparing Grignard reactants from the corresponding substituted phenyl halides by known techniques (see e.g. M. S. Kharash et al.: Grignard Reactions of Nonmetallic Substances, Ed., Prentice-Hall Inc. (1954) pp. 5–90).

The organometallic compounds of the formula (III) are prepared for example according to Houben-Weyl: Methoden der Organischen Chemie, XIII/1, 134–159 (1970).

The dihydroxybenzophenones of the formula (IV) are prepared for example by Friedel-Crafts ketone synthesis of Fries reaction (G. A. Olah: Friedel-Crafts and Related Reactions, III/1, Ed., Interscience Publishers, 1–63, 499–511 (1964)).

According to a preferred embodiment of process variants (a) provided by the invention 2',4'-dihydroxy-propiophenone is reacted with an aryl magnesium halide of the formula (II), preferably aryl magnesium chloride, in a dry organic solvent. Of the Grignard reactant at least three molar equivalents are used in the reaction. The reaction is carried out in aprotic organic solvents, for example in aliphatic ethers such as diethyl ether, di-n-propyl ether, diethylene glycol dimethyl ether; alicyclic ethers such as tetrahydrofurane, dioxane; aliphatic or aromatic hydrocarbons such as ligroin, benzene, toluene, xylene or optional mixtures of these solvents.

The reaction temperature may range from −30° C. up to the boiling point of the solvent, and preferably is between −10° C. and 100° C.

When the reaction is complete, the Grignard complex is decomposed with a dilute aqueous mineral acid, for example acetic acid or preferably with an aqueous solution of ammonium chloride, and the compound of the formula (I) formed is isolated. The product can be purified for example by recrystallization.

According to process variant (b) 2',4'-dihydroxy-propiophenone is reacted with an alkali metal-organic compound of the formula (III), preferably with the corresponding substituted phenyl lithium, under anhydrous conditions, in an inert organic solvent. The compounds of the formula (III) are employed in an amount of at least three molar equivalents. As organic solvents aprotic solvents, e.g. ether, tetrahydrofuran, dioxane, benzene, toluene, xylene, hexane, dimethyl sulfoxide or hexamethyl phosphorus amide or a mixture of these solvents are employed. The reaction temperature may vary between −60° C. and 100° C., preferably −40° C. and 80° C. The product is isolated and, if desired, purified as described in connection with process variant (a).

According to a preferred embodiment of process variant (c) a benzophenone of the formula (IV) is reacted with ethyl magnesium bromide or ethyl magnesium iodide or ethyl lithium, in the presence of a dry organic solvent. The benzophenone of the formula (IV) is reacted with at least three molar equivalents of the ethyl magnesium halide or ethyl lithium. Preferably ethers, aliphatic and aromatic hydrocarbons or mixtures thereof are used as solvents. The reaction is performed at a temperature between −60° C. and the boiling point of the solvent, preferably between −40° C. and 100° C.

The reaction mixture is then decomposed with a dilute mineral or organic acid, or preferably with an aqueous solution of ammonium chloride, and the obtained compound of the formula (I) is isolated. The product may be purified for example by treatment with a solvent, boiling, trituration, precipitation, chromatography, crystallization or by a combination of two or more of these techniques.

Process variants (a) to (c) are preferably carried out in inert gas atmosphere, such as argon or nitrogen.

The new compounds of the formula (I) possess valuable pharmacological properties. More particularly, they are suitable for the treatment of acute ethanolic intoxication, therefore can be widely used in therapy. The acute ethanolic intoxication is characterized in euophoria, general stimulation, ataxia, somnolence, paralytic condition, etc. The dangers of this toxic, pathological condition are well known and cannot be neglected, since the intoxicated person is a threat to his environment (e.g. driving while intoxicated) and exposes his own health to danger. The acute alcoholic intoxication is a substantial "risk factor" of cerebral ischaemic infarcts (Hillbom, M. et al: Lancet 2, 1181 (1978); Stroke, 12, 422 (1981)). Ethanolic intoxication has no satisfactory antidote. α-Methyl-para-tyrosine normalizes the ethanolic locomotoric hyperactivity on mice in a dose range, in which it decreases the spontaneous locomotoric activity of animals (Carlsson, A. et al.: Psychopharm., 26, 307 (1972)). The narcotizing effect of alcohol is reduced by stimulants but these agents prolong the motoric incoordination (ataxia) (Wallagsen, H. et al.: Actions of alcohol, Amsterdam; Elsevier 1970; Rech, R. H. et al.: Ann. N.Y. Acad. Sci., 28, 426 (1976); Todzy I. et al.: Psychopharm., 59, 143 (1978)). The alcoholic intoxication, narcosis is shortened by L-cysteine (Sprince, H. et al.: Agents and Actions, 4, 125 (1974); Nagasawa, H. T. et al.: Life Sci.: 17, 707 (1975)), which is used as a reference compound for alcoholic narcosis period tests.

The change of ethanolic narcosis period was tested on Hann.-Wistar rats of both sexes weighing 160 to 180 g. each, which were fasted for 16 hours prior to treatment. Groups of ten were treated with various doses of a test compound of the formula (I), orally. One hour after treatment the rats were administered a 3.5 g./kg. dose of ethanol intraperitoneally. The narcosis period of the animals was measured from the elapse of the righting reflex until a spontaneous correction of the body position. The average of the narcosis period and the percentage difference related to the control were calculated. The results are shown in Table 1.

Abbreviations:

$\bar{x} \pm S.E.$ = mean value ± standard error n = number of animals

The control group was treated with placebo and a 3.5-mg./kg. dose of ethanol. Control narcosis period: $99.6 \pm 6.55$ ($\bar{x} \pm S.E.$) min.

A = 4-[1-(3-trifluoromethylphenyl)-1-hydroxypropyl]-resorcin

TABLE 1

| Compound | Dose (mg/kg) | Ethanolic narcosis period ($\bar{x} \pm$ S.E. %) | LD$_{50}$ (mg/kg) p.o. | n |
| --- | --- | --- | --- | --- |
| A | 0.3 | 70 ± 11.4 | 1250.0 | 10 |
|   | 1.0 | 60 ± 9.2 |  | 10 |
|   | 5.0 | 36 ± 4.0 |  | 10 |
|   | 20.0 | 30 ± 5.5 |  | 10 |
| L-cysteine | 500.0 | 63 ± 4.2 | 1890.0 | 10 |
| Control |  | 100 ± 6.6 |  | 10 |

As appears from the above data, the compounds of the formula (I) effectively shorten the ethanolic narcosis period, their effect is dose-dependent, unlike that of L-cysteine. The compounds further reduce the depressing effect of alcohol on the central nervous system. The compounds according to the invention show the same activity as L-cysteine in a 500-times lower dose, while they are superior in about 100-times lower doses. In addition to its CNS depressing effect, ethanol, due to its stimulating effect, causes hyperactivity.

The change of ethanolic locomotor activity was tested on BALB/c mice of both sexes, weighing 16 to 18 g. each. Groups of 15 were treated with a 40 mg./kg. oral dose of the test compound 60 minutes prior to the administration of placebo and 2 g./kg. ethanol, respectively (i.p.).

The control animals were treated with placebo. The locomotor activity of the animals was measured for two hours with an Animex BSE motimeter. The results, expressed in percentage of the control, are set forth in Table 2.

TABLE 2

| Compound | Dose (mg/kg) | Ethanol | Total locomotor motion/2 hours in % of the control | n |
| --- | --- | --- | --- | --- |
| Placebo control* | — | — | 100 ± 8.8 | 15 |
| Ethanol + placebo |  | 2000 | 180 ± 10.3 | 15 |
| A + placebo | 40 |  | 110 ± 10.3 | 15 |
| A + ethanol | 40 | 2000 | 98 ± 9.5 | 15 |

*Placebo control $\bar{x} \pm$ S.E. = 2941.5 ± 258.11 total motion/2 hours

The results show that the compounds provided by the present invention have a normalizing effect on hyperactivity induced by ethanol, the test animals treated with the compounds according to the invention and ethanol show the same locomotor activity as the control animals treated with placebo. At the same time, the compounds have no effect on the spontaneous locomotor activity of the animals.

The effect of the compounds of the formula (I) on ataxia induced by ethanol was observed in rotarod test. Previously trained and selected BALB/c mice weighing 16 to 18 g. each were treated with a 40 mg./kg. dose of the compound to be tested orally, one hour before the intraperitoneal administration of a 2.5 g./kg. dose of ethanol. The number of the animals remaining on the rods 60, 90 and 120 minutes, resp., after treatment with ethanol was determined. The animals having an intact coordination could stay at the rod as long as 120 minutes. The results obtained are shown in Table 3. The test was carried out on groups of ten.

TABLE 3

| Compound | Dose (mg/kg) | | Animals remaining on the rotating rod (%) | | |
|---|---|---|---|---|---|
| | Compound | Ethanol | 60 | 90 | 120 min. |
| Ethanol | | 2500 | 10 | 40 | 50 |
| A + Ethanol | 40 | 2500 | 40 | 60 | 100 |
| A | 40 | | 100 | 100 | 100 |

As appears from the above results, the compounds according to the invention have no influence on the motor coordination of the animals when administered in a dose of 40 mg./kg., at the same time, effectively reduce the ataxia induced by ethanol and antagonize the depressing effect of ethanol on the central nervous system.

The compounds of the formula (I) showed no central nervous activity when tested with the following methods: electroshock (Swinyard, E. A., Brown, W. C., Goodman, L. S.: J. Pharmacol. Exp. Ther. 106, 319 (1952)), metrazole spasm (Everett, G. M., Richards, R. K.: J. Pharmacol. Exp. Ther. 81, 402 (1944)), thiosemicarbazide spasm (Di Vanzo, J. P., Greig, M. E., Cormin, M. A.: Amer. J. Physiol. 201, 833 (1961)), strychnine spasm (Kerley, T. L., Richards, A. G., Begley, R. W., Abreu, B. B., Wesver, L. C.: J. Pharmacol. Exp. Ther. 132, 360 (1961)), nicotine spasm (Stone, C. A., Mecklenburg, K. L., Torhans, M. L.: Arch. Int. Pharmacodyn. 117, 419 (1958)), physostigmine lethality preventing effect (Nose, T. and Kojima, M.: Europ. J. Pharmacol. 10, 83 (1970)), yohimbine potentiation effect (Quinton, R. M.: Brit. J. Pharmacol. 21, 51 (1963)), and analgesic activity (Bianchi, C., Franceschini, J.: Brit. J. Pharm. Chemother., 9, 280 (1954)).

The acute toxicity of the compounds according to the invention was tested on male Hann.-Wistar rats each weighing 160 to 180 g. The animals were treated with various doses of the test compounds orally, and the dose resulting in the perish of 50% of the animals was calculated by probite analysis from the %-age of the perished animals. The animals were observed for 14 days. The results ($LD_{50}$) are set forth in Table 1.

The results show that the compounds provided by the invention have a favourable influence on the behaviours altered by ethanol. They antagonize both the stimulating and the depressing effect of ethanol on the central nervous system, shorten the time in which the animals become intact again, have a favorable toxicity and a wide therapeutic spectrum.

The pharmaceutically active compounds according to the invention can be used in therapy in the form of pharmaceutical compositions which are formulated as preparations suitable for oral, rectal and/or parenteral administration. For oral administration tablets, dragées or capsules are prepared. The oral formulations contain as a vehicle e.g. lactose or starch, as an excipient or granulation aid e.g. gelatine, carboxymethyl cellulose sodium, methyl cellulose, polyvinyl pyrrolidone or starch gum, as a disintegrating substance e.g. potato starch or microcrystalline cellulose, ultraamylopectin or formaldehyde casein, etc. The formulations may contain adhesives and lubricants such as talc, colloidal silica, stearin, calcium or magnesium stearate, etc. as well.

Tablets are prepared for example by wet granulation and subsequent pressing. A mixture of the active ingredient and the vehicle and optionally a part of the disintegrating agent are granulated with an aqueous, alcoholic or aqueous-alcoholic solution of the excipients in a suitable equipment, and the granulate is dried. The remaining portion of the disintegrating substance, lubricant, antiadhesive or optional further additives is then added to the granules, and the mixture is pressed to tablets. If desired, the tablets are prepared with a dividing line, which facilitates administration. Tablets can be prepared also from a mixture of the active ingredient and suitable additives by direct pressing.

If desired, the tablets can be converted into dragées, using protecting, flavoring agents and pigments generally known for the preparation of pharmaceutical compositions, e.g. sugar, cellulose derivatives (methyl or ethyl cellulose, carboxymethyl cellulose sodium, etc.), polyvinylpyrrolidone, calcium phosphate, calcium carbonate, food pigments, food oil varnishes, aroma substances, iron oxide pigments, etc.

Capsules are prepared by filling a mixture of the active ingredients and additives into suitable capsules.

For rectal administration the compositions are formulated as suppositories, which contain in addition to the active ingredient a carrier mass, called adeps pro suppository. Suitable carriers include vegetable fats, e.g. hardened vegetable oils, triglycerides of fatty acids having from 12 to 18 carbon atoms, preferably Witepsol (a registered trade mark). The active ingredient is homogeneously distributed in the melted carrier mass, and suppositories are prepared by casting.

For parenteral administration injectable preparations are prepared. To prepare an injectable solution, the active ingredient is dissolved in distilled water and/or various organic solvent, e.g. glycol ethers, optionally in the presence of dissolution aids, e.g. polyoxyethylene sorbitan monolaurate, monooleate or monostearate (Tween 20, Tween 60, Tween 80). The injectable solutions may contain also various additives, e.g. preserving agents such as benzyl alcohol, p-oxy-benzoic acid methyl or propyl ester, benzalkonium chloride or phenyl mercuri borate, etc., antioxidants such as ascorbic acid, tocopherol, sodium pyrosulfate and optionally complexing agents to bind metal traces such as ethylene diamine tetraacetate, buffers to adjust the pH and optionally local anaesthetics such as lidocaine. The injection solutions are filtered, filled into ampoules and sterilized. The daily dose, depending on the state of the patient, varies between 0.1 and 300.0 mg./kg., preferably 2.0 and 160 mg./kg., which is preferably administered in more smaller dose units.

The invention will be further illustrated by the following Examples but it is not intended to limit the scope of the invention to the Examples.

EXAMPLE 1

4-[1-(3-Trifluoromethylphenyl)-1-hydroxypropyl]-resorcin

To a Grignard reactant prepared from 14.6 g. of magnesium turnings and 135 g. of 3-trifluoromethyl-bromobenzene in 330 ml. of tetrahydrofurane a solution of 16.6 g. of 2',4'-dihydroxy-propiophenone in 83 ml. of tetrahydrofurane is added dropwise, at 50° C., and the mixture is stirred at this temperature for 30 additional minutes. After cooling, the reaction mixture is decomposed with a cold 20% aqueous ammonium chloride solution, with stirring. The phases are separated, the aqueous phase is extracted with tetrahydrofurane, the combined organic phases are washed with a saturated aqueous sodium chloride solution, dried over anhydrous magnesium sulfate, and the solvent is distilled off in vacuo. The residue is decolored with activated carbon in methanol, the solvent is filtered off, and distilled off under reduced pressure. If desired, the product is crystallized from a mixture of ethyl acetate and n-hexane to yield 26.6 g. of the named compound, melting at 137° to 138° C.

Analysis for $C_{16}H_{15}F_3O_3$: Calculated: C 61.53%, H 4.84%, F 18.25%; Found: C 61.71%, H 4.97%, F 18.51%.

EXAMPLE 2

4-[1-(2-Trifluoromethylphenyl)-1-hydroxypropyl]-resorcin

To 2-trifluoromethylphenyl-lithium prepared from 18.9 g. of n-butyl-lithium and 65.2 g. of 2-bromobenzotrifluoride in 480 ml. of dry ether, a solution of 8.3 g. of 2',4'-dihydroxy-propiophenone in 85 ml. of dry ether is added dropwise, with stirring at a temperature between 0° C. and −5° C. The reaction mixture is stirred at room temperature for further two hours. After cooling the mixture is poured onto a 10% solution of ammonium chloride in ice water. The phases are separated and the aqueous phase is extracted with ether. The organic phase is washed to neutral with water, dried over anhydrous magnesium sulfate, decolored with activated carbon, filtered, and ether is distilled off under reduced pressure. As a residue 15 g. of an oily product are obtained, which is then chromatographed on a silica gel column by elution with dichloromethane. Dichloromethane is then distilled off under reduced pressure, and the solid residue is crystallized from a mixture of n-hexane and ethyl acetate to yield 6.9 g. of the named compound, melting at 143° to 144° C.

Analysis for $C_{16}H_{15}F_3O_3$: Calculated: C 61.53%, H 4.84%, F 18.25%; Found: C 61.75%, H 5.02%, F 18.33%.

EXAMPLE 3

4-[1-(4-Fluorophenyl)-1-hydroxypropyl]-resorcin

Ethyl magnesium iodide is prepared from 4.8 g. of magnesium turnings and 31.2 g. of ethyl iodide in 80 ml. of dry ether. To a cool solution of the Grignard compound a solution of 7.9 g. of 4-fluoro-2',4'-dihydroxybenzophenone in 80 ml. of dry ether is added dropwise, taking care that the temperature does not exceed −5° C. The reaction mixture is then stirred at 0° C. for 30 minutes and subsequently under reflux for one hour. The mixture is cooled and poured on a solution of ammonium chloride in ice water. The ethereal phase is separated and the aqueous phase is extracted with ether. The organic phases are combined, washed to neutral with water, and dried over anhydrous magnesium sulfate. After filtration the solvent is distilled off under reduced pressure. Crystallization of the solid residue from a mixture of n-hexane and ethyl acetate yields 5.1 g. of the named compound, melting at 126° C.

Analysis for $C_{15}H_{15}FO_3$: Calculated: C 68.69%, H 5.76%, F 7.24%; Found: C 68.85%, H 5.93%, F 7.44%.

EXAMPLE 4

4-[1-(2-Methoxyphenyl)-1-hydroxypropyl]-resorcin

To an ethyl lithium solution prepared from 29.4 g. of ethyl bromide and 3.7 g. of lithium in 33o ml. of dry ether, under argon atmosphere, which is cooled to −10° C., a solution of 11 g. of 2-methoxy-2',4'-dihydroxy-benzophenone in 60 ml. of dry tetrahydrofurane is added dropwise, taking care that the temperature does not exceed −5° C. Thereafter the reaction mixture is stirred at 0° C. for 30 minutes and then at room temperature for two hours. The reaction mixture is decomposed with a 10% aqueous ammonium chloride solution, the phases are separated, and the aqueous phase is extracted with ether. The combined ethereal phases are washed to neutral with water, dried over anhydrous magnesium sulfate, filtered, and the solvent is distilled off in vacuo, after decoloring with activated carbon. Crystallization of the solid residue from a mixture of n-hexane and ethyl acetate yields 8.3 g. of the named compound, melting at 141° to 142° C.

Analysis for $C_{16}H_{18}O_4$: Calculated: C 70.05%, H 6.61%; Found: C 70.21%, H 6.76%.

Similarly there can be prepared the following compounds by proper selection of the starting substances:

4-[1-(4-chlorophenyl)-1-hydroxypropyl]-resorcin, melting point: 88° C.

Analysis for $C_{15}H_{15}ClO_3$: Calculated: C 64.63%, H 5.42%, Cl 12.72%; Found: C 64.42%, H 5.54%, Cl 12.88%.

4-[1-(4-trifluoromethylphenyl)-1-hydroxypropyl]-resorcin,

Analysis for $C_{16}H_{15}F_3O_3$: Calculated: C 61.53%, H 4.84%, F 18.25%; Found: C 61.63%, H 4.78%, F 18%.

4-[1-(3-chlorophenyl)-1-hydroxypropyl]-resorcin, melting point: 144° to 145° C.

Analysis for $C_{15}H_{15}ClO_3$: Calculated: C 64.63%, H 5.42%, Cl 12.72%; Found: C 64.51%, H 5.60%, Cl 12.95%.

4-[1-(2,5-dimethylphenyl)-1-hydroxypropyl]-resorcin, melting point: 110° C.

Analysis for $C_{17}H_{20}O_3$: Calculated: C 74.97%, H 7.40%; Found: C 75.10%, H 7.33%.

4-[1-(4-trifluoromethylphenyl)-1-hydroxypropyl]-resorcin, melting point: 141° to 142° C.

Analysis for $C_{16}H_{15}F_3O_3$: Calculated: C 61.53%, H 4.84%, F 18.25%; Found: C 61.58%, H 4.90%, F 18.21%.

EXAMPLE 5

The new compounds according to the invention can for example be converted into the following pharmaceutical compositions.

Tablets

Composition of a single tablet:
active ingredient—100.0 mg.
lactose—184.0 mg.
potato starch—80.0 mg.
polyvinyl pyrrolidone—8.0 mg.
talc—12.0 mg.
magnesium stearate—2.0 mg.
aerosil (colloidal silica)—2.0 mg.
ultraamylopectin—12.0 mg.

From the above ingredients 400-mg. tablets are prepared by wet granulation and subsequent pressing.
Active ingredient: 4-[1-(3-trifluoromethylphenyl)-1-hydroxypropyl]-resorcin

Dragées

Tablets as described above are coated with a layer prepared from sugar and talc in a known manner. Dragées are polished with a mixture of bee wax and carnauba wax. Weight of a dragée: 500.0 mg.

Capsules

Composition of a capsule:
active ingredient—50.0 mg.
lactose—100.0 mg.
talc—2.0 mg.
potato starch—30.0 mg.
cellulose (microcrystalline)—3.0 mg.

The active ingredient is thoroughly admixed with the additives, the mixture is passed through a 0.32-mm. sieve, and filled into hard gelatine capsules (size 4).
Active ingredient: 4-[1-(3-trifluoromethylphenyl)-1-hydroxypropyl]-resorcin

Suppositories

Composition of a suppository:
active ingredient—100.0 mg.
lactose—200.0 mg.
basic substance (e.g. Witepsol H)—1700.0 mg.

The basic substance is melted and is then cooled to 35° C. The active ingredient is thoroughly blended with the lactose, and the mixture is homogenized in the basic substance in a homogenizer. The obtained mass is poured into cool moulds. One suppository weights 2000 mg.
Active ingredient: 4-[1-(3-trifluoromethylphenyl)-1-hydroxypropyl]-resorcin

Suspension

Composition of 100 ml. of suspension:
active ingredient—1.00 g.
sodium hydroxide—0.26 g.
citric acid—0.30 g.
nipagin (4-hydroxybenzoic acid methyl ester sodium salt)—0.10 g.
Carbopol 940 (polyacrylic acid)—0.30 g.
ethanol (96%)—1.00 g.
raspberry aroma—0.60 g.
sorbite (70% aqueous solution)—71.00 g.
distilled water—ad 100.00 ml.

To a solution of nipagin and citric acid in 20 ml. of distilled water Carbopol is added portionwise, with vigorous stirring, and the solution is allowed to stand for 10 to 12 hours. Thereafter a solution of the above amount of sodium hydroxide in 1 ml. of distilled water is added dropwise, followed by dropwise addition of an aqueous solution of sorbite and an ethanolic raspberry aroma solution, with stirring. Active ingredient is added in small portions, and the mixture is homogenized. The suspension is supplemented with distilled water ad 100 ml., and the suspension syrup is passed through a colloidal mill.

Active ingredient: 4-[1-(3-trifluoromethylphenyl)-1-hydroxypropyl]-resorcin

We claim:

1. A compound of the formula (I)

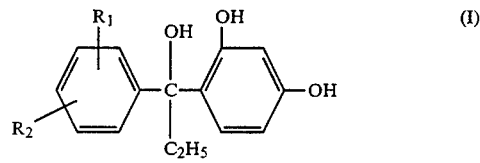

wherein $R_1$ and $R_2$ independently represent hydrogen, halogen, trihalomethyl, alkyl having from one to 3 carbon atoms or alkoxy having from one to 3 carbon atoms.

2. A compound selected from the following group:
4-[1-(3-trifluoromethylphenyl)-1-hydroxypropyl]-resorcin,
4-[1-(2-trifluoromethylphenyl)-1-hydroxypropyl]-resorcin,
4-[1-(4-fluorophenyl)-1-hydroxypropyl]-resorcin,
4-[1-(2-methoxyphenyl)-1-hydroxypropyl]-resorcin,
4-[1-(4-chlorophenyl)-1-hydroxypropyl]-resorcin,
4-[1-(3-chlorophenyl)-1-hydroxypropyl]-resorcin,
4-[1-(2,5-dimethylphenyl)-1-hydroxypropyl]-resorcin, and
4-[1-(4-trifluoromethylphenyl)-1-hydroxypropyl]-resorcin.

3. A pharmaceutical composition containing a resorcin derivative of the formula (I) as claimed in claim 1, wherein $R_1$ and $R_2$ are as defined in claim 1, together with pharmaceutically acceptable carriers and/or auxiliary substances.

4. A method of treating acute ethanolic intoxication which comprises the step of administering to an affected subject an effective amount of a compound as defined in claim 1.

* * * * *